United States Patent
Yamazaki

(10) Patent No.: US 10,669,226 B2
(45) Date of Patent: Jun. 2, 2020

(54) POLYMERIZABLE TRIPTYCENE DERIVATIVE COMPOUND

(71) Applicant: SEED CO., LTD., Tokyo (JP)

(72) Inventor: Yoshiko Yamazaki, Tokyo (JP)

(73) Assignee: SEED CO., LTD., Tokyo (JP)

(*) Notice: Subject to any disclaimer, the term of this patent is extended or adjusted under 35 U.S.C. 154(b) by 0 days.

(21) Appl. No.: 16/321,024

(22) PCT Filed: Aug. 2, 2017

(86) PCT No.: PCT/JP2017/027978
§ 371 (c)(1),
(2) Date: Jan. 27, 2019

(87) PCT Pub. No.: WO2018/025892
PCT Pub. Date: Feb. 8, 2018

(65) Prior Publication Data
US 2019/0177263 A1    Jun. 13, 2019

(30) Foreign Application Priority Data
Aug. 3, 2016 (JP) ................. 2016-152953

(51) Int. Cl.
*C07C 69/54* (2006.01)
*C07C 229/34* (2006.01)
*C07C 57/50* (2006.01)
*C07C 59/72* (2006.01)

(52) U.S. Cl.
CPC .............. *C07C 69/54* (2013.01); *C07C 57/50* (2013.01); *C07C 59/72* (2013.01); *C07C 229/34* (2013.01); *C07C 2603/90* (2017.05); *Y02P 20/55* (2015.11)

(58) Field of Classification Search
CPC ....... C07C 57/50; C07C 69/54; C07C 229/34; C07C 2603/90; C07C 59/72; Y02P 20/55
See application file for complete search history.

(56) References Cited

U.S. PATENT DOCUMENTS

| 3,370,092 | A | 2/1968 | Kornfeld |
| 6,605,693 | B1 | 8/2003 | Becker et al. |
| 2011/0237804 | A1 | 9/2011 | Tanaka et al. |

FOREIGN PATENT DOCUMENTS

| JP | 60-081148 | 5/1985 |
| JP | 63-115832 | 5/1988 |
| JP | 2004-067816 | 3/2004 |
| JP | 2006-111571 | * 4/2006 |
| JP | 2006-187225 | 7/2006 |
| JP | 2008-075047 | 4/2008 |
| JP | 2008-308433 | 12/2008 |
| JP | 2011-246365 | 8/2011 |
| JP | 2013-223458 | 10/2013 |
| JP | 2014-178712 | 9/2014 |

OTHER PUBLICATIONS

Brunovlenkaya, I. I. et al., Aromatic hydrocarbons. LXII. Deamination of 9, 10-bis(aminomethyl) triptycene, Zhurnal Organicheskoi Khimii, 1978, vol. 14, No. 10, p. 2141-2144.
Brunovlenkaya, I. I. et al., Aromatic hydrocarbons. LXIII. Intramolecular cyclization in the triptycene series, Zhurnal Organicheskoi Khimii, 1979, vol. 15, No. 7, p. 1502-1506.
Notification concerning transmittal of international preliminary report on patentability (Form PCT/IB/326), International preliminary report on patentability (Form PCT/IB/373) (6 pages).
Notification of transmittal of translation of the international preliminary report on patentability (Form PCT/IB/338), and Translation of International preliminary report on patentability (Form PCT/IB/373) (8 pages).
International Search Report of corresponding PCT application PCT No. PCT/JP2017/027978 International filing date: Sep. 12, 2017(Japanese version and English Version).
Hoffmeister, E. et al., Triptycene polymers, Journal of Polymer Science, Part A-1: Polymer Chemistry, 1969, vol. 7, No. 1, p. 55-72.
Barros, S. A. et al., Bridgehead-Substituted Triptycenes for Discovery of Nucleic Acid Junction Binders, Organic Letters, 2016, vol. 18, No. 10, p. 2423-2426.
Brunovlenkaya, I. I. et al.,Aromatic hydrocarbons. LXIII. Intramolecular cyclization in the triptycene series, Zhurnal Organicheskoi Khimii, 1979, vol. 15, No. 7, p. 1502-1506.
Cristol, S. J. et al., Bridged polycyclic compounds. LXI. Synthesis and some properties of tribenzobicyclo[3.2.2] nonatriene (homotriptycene) and derivatives, Journal of Organic Chemistry, 1970, vol. 35, No. 7, p. 2357-2361.

* cited by examiner

*Primary Examiner* — Yevgeny Valenrod
*Assistant Examiner* — Blaine G Doletski
(74) *Attorney, Agent, or Firm* — JMB Davis Ben-David

(57) ABSTRACT

It is an objective of the present invention to provide a novel polymerizable triptycene derivative that has a structure in which three benzene rings arranged at the axis formed by barrelene of the triptycene skeleton can rotate evenly and that has hydrophilicity imparted to it as compared to any of the prior art triptycene derivatives and is thus highly useful in functional materials.
The above objective is achieved by the polymerizable triptycene derivative having substituents with an unsaturated bonding functional group at position 9 and/or position 10 of the triptycene skeleton, the polymerizable triptycene derivative having two carboxyl groups and the polymerizable triptycene derivative having one carboxyl group and one amino group.

3 Claims, No Drawings

POLYMERIZABLE TRIPTYCENE DERIVATIVE COMPOUND

CROSS-REFERENCE TO RELATED APPLICATION

This is the U.S. National Stage of International Patent Application No. PCT/JP2017/027978 filed Aug. 2, 2017, which was published in Japanese under PCT Article 21(2), and which claims the benefit of priority to Japanese Patent Application No. 2016-152953, filed Aug. 3, 2016, the disclosure of which is incorporated herein by reference in its entirety.

TECHNICAL FIELD

The present invention relates to a triptycene derivative having a substituted triptycene structure.

BACKGROUND ART

A polymer compound can be obtained by polymerization of one or combination of two or more of polymerizable compounds such as (meth)acrylic acids and their derivatives as monomer components or by polycondensation of compounds having a dicarboxylic acid or compounds having an amino group and a carboxylic group within the molecules.

The characteristics of the polymer compound can vary widely depending on the monomer compounds used as constituent materials or their combinations. Hence, it is necessary to take into consideration such combinations of monomer compounds used as constituent materials or provision of novel monomer compounds for use as constituent materials in order to obtain polymer compounds having new characteristics or polymer compounds having some of their known characteristics improved. To provide novel monomer compounds, known compounds may be chemically modified at specific sites or polymerizable functional groups may be added.

Triptycene is an aromatic hydrocarbon having a paddle wheel-like structure in which three benzene rings are arranged in a manner similar to paddles of a paddle wheel to give $D_{3h}$ symmetry. Because of such a structure, application of triptycene in various functional materials has been contemplated. Several triptycene derivatives that have a triptycene structure (skeleton) are also known.

Among known such compounds are, for example, compounds formed by ring fusion of triptycene skeleton with further other ring structures (See Patent Document 1 below, the disclosure of which is incorporated herein by reference in its entirety), optically active triptycene derivatives obtained by asymmetric acylation with enzymes (See Patent Document 2 below, the disclosure of which is incorporated herein by reference in its entirety), and optically active triptycene derivatives obtained by reacting a mixture of optical isomers of a triptycene derivative having hydrolyzable functional groups with a hydrolase capable of asymmetric hydrolysis (See Patent Document 3 below, the disclosure of which is incorporated herein by reference in its entirety).

Also known are a photoresist substrate and a photoresist composition in which a triptycene derivative with a specific structure are oriented (See Patent Document 4 below, the disclosure of which is incorporated herein by reference in its entirety); a triptycene ring-containing liquid crystal compound that exhibits a good compatibility with other liquid crystal compounds, has a small phase shift or a small chromatic dispersion of optical anisotropy, and has polymerizability (See Patent Document 5 below, the disclosure of which is incorporated herein by reference in its entirety); a triptycene group-containing polymer electroluminescence material having, optionally substituted, vinylene group, ethynylene group, arylene group, heteroarylene group and spirobifluorene group (See Patent Document 6 below, the disclosure of which is incorporated herein by reference in its entirety); a triptycene-containing compound that is one of compounds having a polymerizable group and a 1,4-dimethylenecyclohexane backbone, and that has a liquid crystal phase and exhibits a good compatibility with other liquid crystal compounds and organic solvents (See Patent Document 7 below, the disclosure of which is incorporated herein by reference in its entirety); and a triptycene-containing compound that is one of liquid crystal display element compounds that are composed of a photopolymerizable monomer and/or oligomer selected from a polyimide consisting of a diamine and a tetracarboxylic acid dianhydride or a polyamic acid derivative, a precursor of the polyimide (See Patent Document 8 below, the disclosure of which is incorporated herein by reference in its entirety).

Further known is a triptycene derivative having a structure consisting of a barrelene having a plurality of unsaturated polymerizable functional groups attached thereto, including a triple bond-containing functional group and a double bond-containing functional group (See Patent Document 9 below, the disclosure of which is incorporated herein by reference in its entirety).

PRIOR ART DOCUMENT

Patent Document

Patent Document 1: JP 2011-207792 A
Patent Document 2: JP 2013-223458 A
Patent Document 3: JP 2006-187225 A
Patent Document 4: JP 2008-308433 A
Patent Document 5: JP 2006-111571 A
Patent Document 6: JP 2002-539286 A
Patent Document 7: JP 2011-246365 A
Patent Document 8: JP 2014-178712 A
Patent Document 9: JP 2008-075047 A

SUMMARY OF INVENTION

Technical Problem

Because most of the prior art triptycene derivatives have a structure in which a polymerizable group for forming a polymer extension chain has been incorporated into an aromatic ring of the triptycene skeleton, it is likely that the rotation of the polymer about an axis formed by barrelenes each having fused three benzene rings is hindered. On the other hand, such a rotation is less likely to be hindered in the triptycene derivative as described in Patent Document 9 since unsaturated polymerizable functional groups are at positions 9 and 10 of the triptycene.

However, the hydrophobic nature of alkenyl and alkynyl groups used as the unsaturated polymerizable functional groups in the triptycene derivative as described in Patent Document 9, as well as hydrophobic nature of triptycene itself, makes the overall triptycene derivative as described in Patent Document 9 hydrophobic. Because of this characteristic, the triptycene derivative as described in Patent Document 9 has limited applications in compositions for use as functional materials and is thus less useful.

In view of the above-identified problems, it is an objective of the present invention to provide a novel polymerizable triptycene derivative that has a structure permitting even rotation of the three benzene rings arranged about the axis formed by barrelenes of the triptycene backbone and that has hydrophilicity imparted to it as compared to any of the prior art triptycene derivatives and is thus highly useful in functional materials.

Solution to Problem

In an effort to provide the above-described novel polymerizable triptycene derivatives, the present inventors have focused on the type and attached positions of polymerizable functional groups involved in the polymerization reaction. The present inventors have postulated that in order for the three benzene rings to rotate evenly, it is important that the three benzene rings rotate about the barrelene to which they are attached. The present inventors have further postulated that a polymerizable triptycene derivative having compatibility with other hydrophilic compounds can be provided by selecting hydrophilic functional groups as the polymerizable functional groups to be introduced.

Based on the above-described considerations, the present inventors have conducted extensive studies and after many trials and failures, have succeeded in producing a compound that has hydrophilic polymerizable functional groups at position 9 and/or position 10 of the triptycene skeleton. This compound is a polymerizable triptycene derivative having a structure that permits even rotation of the three benzene rings arranged about the axis formed by barrelene in the triptycene skeleton and has hydrophilicity imparted to it as compared to any of the prior art polymerizable triptycene derivatives. Thus, the compound can serve as a highly useful functional material. These findings and successful examples have ultimately led to the completion of the present invention.

According to one embodiment of the present invention, there is provided a polymerizable triptycene derivative represented by the following general formula (1):

[Chemical Formula 1]

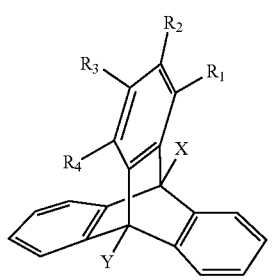

(1)

(wherein
$R_1$ to $R_4$ are each independently a substituent selected from the group consisting of hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group, with the proviso that adjacent substituents may together form a ring;

one of X and Y is a substituent represented by the following general formula (2):

[Chemical Formula 2]

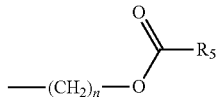

(2)

(wherein n is an integer of 1 to 5; and $R_5$ is a substituent selected from the group consisting of alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group, each having an unsaturated polymerizable functional group;)
and the other of X and Y is a substituent selected from the group consisting of the substituents represented by the general formula (2) above, hydrogen atom and halogen atom, and protected or unprotected hydroxyl group, hydroxylalkyl group, carboxyl group, carboxylalkyl group, amino group, aminoalkyl group, aminocarbonyl group, aminocarbonylalkyl group, alkoxy group, alkoxyalkyl group, alkoxycarbonyl group, alkoxycarbonylalkyl group, formyl group, formylalkyl group, and alkyl group.)

Preferably, the unsaturated polymerizable functional group is an unsaturated polymerizable functional group selected from the group consisting of vinyl group and (meth)acryl group.

According to one embodiment of the present invention, there is provided a polymerizable triptycene derivative represented by the following general formula (1)':

[Chemical Formula 3]

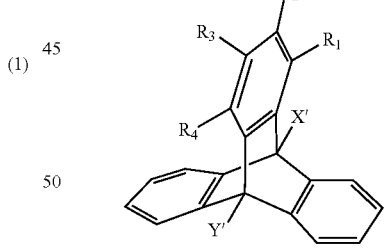

(1)'

(wherein
$R_1$ to $R_4$ are each independently a substituent selected from the group consisting of hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group, with the proviso that adjacent substituents may together form a ring;
one of X' and Y' is a substituent selected from the group consisting of substituents represented by the following general formula (3):

[Chemical Formula 4]

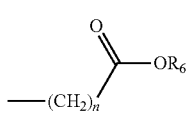

(3)

(wherein n is an integer of 1 to 5; and R₆ is a substituent selected from the group consisting of hydrogen atom and alkyl group having any one of carbons 1 to 3;)
and substituents represented by the following general formula (4):

[Chemical Formula 5]

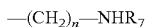

(4)

(wherein n is an integer of 1 to 5; and R₇ is a substituent selected from the group consisting of hydrogen atom and a carbamate protective group;)
and the other of X' and Y' is a substituent selected from the group consisting of hydrogen atom, substituents represented by the general formula (3) above, and substituents represented by the general formula (4) above.)

Advantageous Effects of Invention

Polymerizable triptycene derivatives in one embodiment of the present invention have a structure in which polymerizable functional groups are attached to carbons of barrelene, which forms a main skeleton of triptycene, such that each of the three benzene rings in the triptycene structure can rotate evenly about an axis formed by the barrelene.

Also, polymerizable triptycene derivatives in one embodiment of the present invention are compatible not only with hydrophobic compounds, but also with hydrophilic compounds due to hydrophilic nature of the introduced polymerizable functional groups so that they can be used to produce polymer compositions with a variety of functions not achieved by conventional compounds. In particular, polymerizable triptycene derivatives in one embodiment of the present invention can be used to produce hydrogels swollen by hydration, which were not achieved by any of prior art techniques.

Furthermore, since the three benzene rings in the triptycene structure in the resulting polymer composition can rotate evenly about the axis formed by barrelene, when a material is encapsulated within the polymer composition, it is expected to control the rate and the extent of diffusion of the encapsulated material released from the polymer composition.

DESCRIPTION OF EMBODIMENTS

While polymerizable triptycene derivatives in one embodiment of the present invention will now be described in further details, the technical scope of the present invention is not limited to what is described in this section; rather, the present invention may take various other forms to the extent that its objectives are achieved.

The polymerizable triptycene derivatives in one embodiment of the present invention are represented by the following general formula (1):

[Chemical Formula 6]

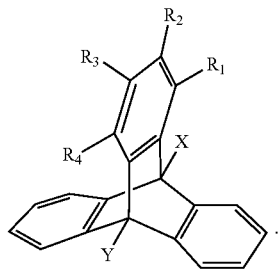

(1)

In the general formula (1), $R_1$ to $R_4$ are each independently selected from the group consisting of hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group. Any adjacent substituents of $R_1$ to $R_4$ may together form a ring.

In the general formula (1), one of X and Y is a substituent represented by the following general formula (2):

[Chemical Formula 7]

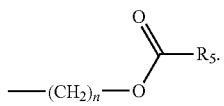

(2)

In the general formula (2), n is an integer of 1 to 5; and $R_5$ is a substituent selected from the group consisting of alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group, each having an unsaturated polymerizable functional group.

The unsaturated polymerizable functional group in the functional group represented by $R_5$ may be any functional group that has an unsaturated bond involved in a polymerization reaction, including, for example, functional groups having a carbon-carbon double bond and a carbon-carbon triple bond. Preferably, the functional group is a vinyl group and a (meth)acryl group having a carbon-carbon double bond. As used herein, the term "(meth)acryl group" collectively refers to functional groups including acryl groups and methacryl groups.

In the general formula (1), one of X and Y is a substituent represented by the general formula (2) and the other substituent is a substituent selected from the group consisting of the substituents represented by the general formula (2) above, hydrogen atom and halogen atom, and protected or unprotected hydroxyl group, hydroxylalkyl group, carboxyl group, carboxylalkyl group, amino group, aminoalkyl group, aminocarbonyl group, aminocarbonylalkyl group, alkoxy group, alkoxyalkyl group, alkoxycarbonyl group, alkoxycarbonylalkyl group, formyl group, formylalkyl group, and alkyl group. The other substituent may be a substituent represented by the general formula (3) or a substituent represented by the general formula (4) as described below. As used herein, the term "protected substituent" is not particularly limited as long as referring to any substituent having any protective group.

The polymerizable triptycene derivatives in another embodiment of the present invention are represented by the following general formula (1)':

[Chemical Formula 8]

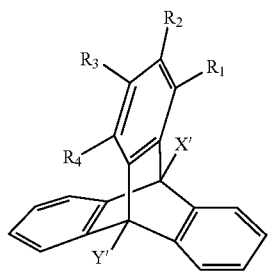

(1)'

$R_1$ to $R_4$ in the general formula (1)' correspond to $R_1$ to $R_4$ in the general formula (1).

One of X' and Y' in the general formula (1') is a substituent selected from the group consisting of substituents represented by the general formula (3) below and substituents represented by the general formula (4) below and the other of X' and Y' is a substituent selected from the group consisting of hydrogen atom, substituents represented by the following general formula (3) and substituents represented by the following general formula (4):

[Chemical Formula 9]

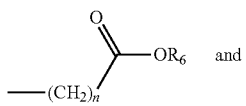

(3)

and

[Chemical Formula 10]

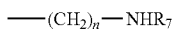

(4)

In the general formula (3), n is an integer of 1 to 5; and $R_6$ is a substituent selected from the group consisting of hydrogen atom and alkyl group having any one of carbons 1 to 3.

In the general formula (4), n is an integer of 1 to 5; and $R_7$ is a substituent selected from the group consisting of hydrogen atom and a carbamate protective group.

Specific embodiments of the polymerizable triptycene derivatives represented by the general formula (1) include, but are not limited to, polymerizable triptycene derivatives in which X and Y are each independently a substituent shown in Table 1 below. In cases where both X and Y are substituents represented by the general formula (2) as in compound (1)-B, they may be an identical substituent or they may be substituents that differ from each other.

TABLE 1

| compound | X | Y |
|---|---|---|
| (1)-A | general formula(2) | hydrogen atom |
| (1)-B | general formula(2) | general formula(2) |

TABLE 1-continued

| compound | X | Y |
|---|---|---|
| (1)-C | general formula(2) | general formula(3) |
| (1)-D | general formula(2) | general formula(4) |

Specific embodiments of the polymerizable triptycene derivatives represented by the general formula (1)' include, but are not limited to, polymerizable triptycene derivatives in which X' and Y' are each independently a substituent shown in Table 2 below. In cases where both X' and Y' are substituents represented by the general formula (3) (i.e., compound (1)'-B) or by the general formula (4) (i.e., compound (1)'-D), they may be an identical substituent or they may be substituents that differ from each other.

TABLE 2

| compound | X' | Y' |
|---|---|---|
| (1)'-A | general formula(3) | hydrogen atom |
| (1)'-B | general formula(3) | general formula(3) |
| (1)'-C | general formula(3) | general formula(4) |
| (1)'-D | general formula(4) | general formula(4) |
| (1)'-E | general formula(4) | hydrogen atom |

In any of the polymerizable triptycene derivatives shown in Tables 1 and 2, $R_1$ to $R_4$ may be all different substituents, or two, three, or all four of them may be an identical substituent.

While the substituent exemplified for $R_1$ to $R_7$ may be not particularly limited as long as any substituent that has a commonly known meaning, for example, it may be a substituent as exemplified below. In addition, the substituent exemplified for $R_1$ to $R_7$ may bear a further substituent. Examples of the further substituent include, but are not particularly limited to, alkyl group, cycloalkyl group, aryl group and heteroaryl group.

Examples of the alkyl group include, but are not limited to, saturated aliphatic hydrocarbon groups, such as methyl group, ethyl group, n-propyl group, isopropyl group, n-butyl group, sec-butyl group, and tert-butyl group. While the alkyl group may have any number of carbons, it preferably has for example from 1 to 20, more preferably from 1 to 8, and still more preferably from 1 to 3 carbons. Examples of the alkyl group bearing a substituent include, but are not limited to, hydroxyalkyl group, aminoalkyl group, carboxyalkyl group, and formylalkyl group.

Examples of the cycloalkyl group include, but are not limited to, saturated alicyclic hydrocarbon groups, such as cyclopropyl group, cyclohexyl group, norbornyl group, and adamantyl group. While the cycloalkyl group may have any number of carbons, it preferably has from 3 to 20 carbons.

Examples of the heterocyclic group include, but are not limited to, alicyclic rings that contain an atom other than carbon atom, such as nitrogen and sulfur atom, including, for example, pyran ring, piperidine ring, cyclic amide. While the heterocyclic group may have any number of carbons, it preferably has from 2 to 20 carbons.

Examples of the alkenyl include, but are not limited to, unsaturated aliphatic hydrocarbon groups having a double bond, such as vinyl group, allyl group, and butadienyl group. While the alkenyl group may have any number of carbons, it preferably has from 2 to 20 carbons.

Examples of the cycloalkenyl group include, but are not limited to, unsaturated alicyclic hydrocarbon groups having a double bond, such as cyclopentenyl group, cyclopentadienyl group, and cyclohexenyl group.

Examples of the alkynyl group include, but are not limited to, unsaturated aliphatic hydrocarbon groups having a triple bond, such as ethynyl group. While the alkynyl group may have any number of carbons, it preferably has from 2 to 20 carbons.

Examples of the alkoxy group include, but are not limited to, functional groups with an aliphatic hydrocarbon group attached via an ether linkage, including, for example, methoxy group, ethoxy group, and propoxy group. While the alkoxy group may have any number of carbons, it preferably has from 1 to 20 carbons. Examples of the alkoxy group bearing a substituent include, but are not limited to, alkoxyalkyl group, alkoxycarbonyl group, and alkoxycarbonylalkyl group.

Examples of the alkylthio group include, but are not limited to, functional groups in which the oxygen atom of their ether bond in alkoxy groups is replaced with a sulfur atom. While the alkylthio group may have any number of carbons, it preferably has from 1 to 20 carbons.

Examples of the arylether group include, but are not limited to, functional groups having an aromatic hydrocarbon group attached via an ether linkage, such as phenoxy group. While the arylether group may have any number of carbons, it preferably has from 6 to 40 carbons.

Examples of the alkylthioether group include, but are not limited to, functional groups in which the oxygen atom of their ether bond in arylether groups is replaced with a sulfur atom. While the arylthioether group may have any number of carbons, it preferably has from 6 to 40 carbons.

Examples of the aryl group include, but are not limited to, aromatic hydrocarbons, such as phenyl group, naphthyl group, biphenyl group, anthracenyl group, phenanthryl group, terphenyl group, and pyrenyl group. While the aryl group may have any number of carbons, it preferably has from 6 to 40 carbons.

Examples of the heteroaryl group include, but are not limited to, 5-membered cyclic aromatic groups with their rings containing one atom other than carbon, such as furanyl group, thiophenyl group, benzofuranyl group and dibenzofuranyl group, and 6-membered cyclic aromatic groups with their rings containing one or more atoms other than carbon, such as pyridyl group and quinolynyl group. While the heteroaryl group may have any number of carbons, it preferably has from 2 to 30 carbons.

Examples of halogen atom include, but are not limited to, fluorine, chlorine, bromine, and iodine.

Each of the carbonyl group, carboxyl group, oxycarbonyl group, carbamoyl group, amino group, formyl group, and phosphine oxide group may bear a substituent, which in turn may bear a further substituent. Examples of the amino group bearing a substituent include, but are not limited to, aminocarbonyl group, and aminocarbonylalkyl group.

Examples of the silyl group include, but are not limited to, functional groups having a silicon atom bonded to them, such as trimethylsilyl group. While the silyl group may have any number of carbons, it preferably has from 3 to 20 carbons. While the silyl may have any number of silicons, it preferably has from 1 to 6 silicons.

Any adjacent substituents of the substituents represented by $R_1$ to $R_4$, that is, $R_1$ and $R_2$, $R_2$ and $R_3$, and/or $R_3$ and $R_4$ may together form a ring (i.e., fused ring). In other words, the fused ring is formed by any adjacent two substituents selected from $R_1$ to $R_4$ (e.g., $R_1$ and $R_2$) that are bound together to form a conjugated or unconjugated fused ring. Examples of the constituent elements involved in the formation of a fused ring include, but are particularly not limited to, carbon atom, nitrogen atom, oxygen atom, sulfur atom, phosphorus atom, and silicon atom. The substituents represented by $R_1$ to $R_4$ may be further fused with another ring.

Examples of the carbamate protective group include, but are not limited to, carbamate protective groups such as tert-butoxycarbonyl group, benzyloxycarbonyl group, 9-fluorenylmethyloxycarbonyl group, 2,2,2-trichloroethoxycarbonyl group, and allyloxycarbonyl group.

More specific embodiments of the polymerizable triptycene derivatives represented by the general formula (1) include, but are not limited to, for example, compounds of the following formulas (14) and (15), where Me in the formula represents methyl group:

[Chemical Formula 11]

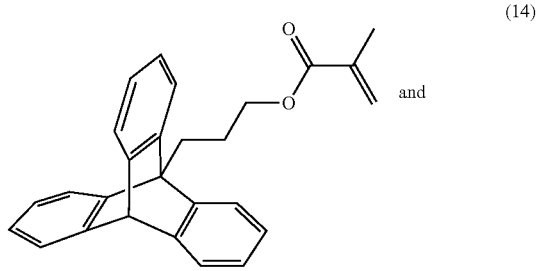

(14)

and

[Chemical Formula 12]

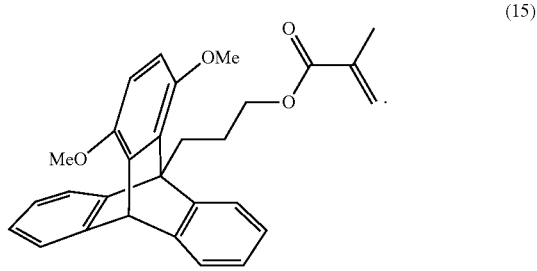

(15)

More specific embodiments of the polymerizable triptycene derivatives represented by the general formula (1)' include, but are not limited to, for example, compounds of the following formulas (16) to (18) and carboxylates thereof:

[Chemical Formula 13]

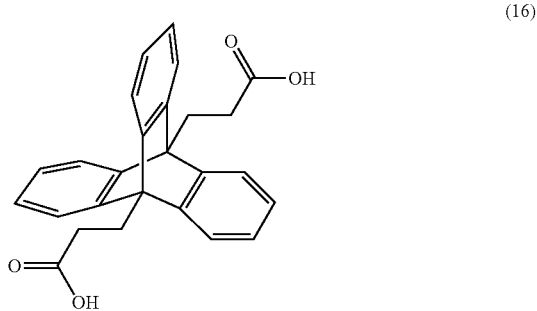

(16)

-continued

[Chemical Formula 14]

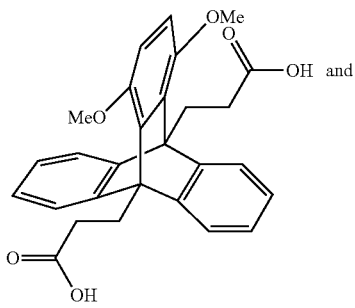

(17)

and

[Chemical Formula 15]

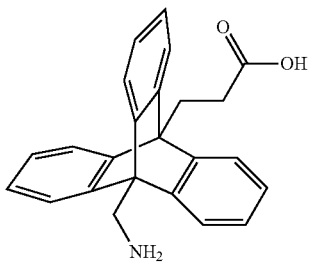

(18)

While the polymerizable triptycene derivative of the present invention may be produced by any method that is not particularly limited, it may be produced for example by using any of the methods described later in Examples or by modifying these methods as desired to obtain desired polymerizable triptycene derivatives.

One embodiment of the production method of a polymerizable triptycene derivative of the general formula (1) includes, but not limited to, a method comprising: subjecting 9-halogen anthracene or 9,10-dihalogen anthracene and an acetal compound having a vinyl group to Heck coupling reaction and hydrolysis; subjecting the resulting reaction product and benzyne to Diels-Alder reaction and, optionally, to a reaction for modifying substituents born by benzyne; subjecting the resulting reaction product to reduction with a metal hydride; and subjecting the resulting reaction product to a reaction with a halogenated (meth)acryloyl to obtain a polymerizable triptycene derivative of the general formula (1).

One embodiment of the production method of a polymerizable triptycene derivative of the general formula (1)' includes, but not limited to, a method comprising: subjecting 9-halogen anthracene or 9,10-dihalogen anthracene and an acetal compound having a vinyl group to a Heck coupling reaction and hydrolysis; subjecting the resulting reaction product and benzyne to a Diels-Alder reaction and, optionally, to a reaction for modifying substituents born by benzyne; and subjecting the resulting reaction product to an alkali treatment and an acid treatment to obtain a polymerizable triptycene derivative of the general formula (1)' in which at least one of X' or Y' is a substituent represented by the general formula (3).

Another embodiment of the production method of a polymerizable triptycene derivative of the general formula (1)' includes, but not limited to, a method comprising: subjecting 9-halogen anthracene or anthracene and an amide compound to a Vilsmeier-Haack reaction; subjecting the resulting reaction product and a primary amine having a carbamate protective group to an amine addition reaction; subjecting the resulting reaction product and benzyne to Diels-Alder reaction and, optionally, to a reaction for modifying substituents born by benzyne; and, optionally, subjecting the resulting reaction product to an alkali treatment and an acid treatment to obtain a polymerizable triptycene derivative of general formula (1)' in which at least one of X' or Y' is a substituent represented by the general formula (4).

Also, a polymerizable triptycene derivative of the general formula (1)' in which at least one of X' and Y' is a substituent represented by the general formula (3) and the other of X' and Y' is a substituent represented by the general formula (4) can be obtained by combining the above-described two embodiments of the production method of a polymerizable triptycene derivative of the above general formula (1)'.

Use of polymerizable triptycene derivatives according to one embodiment of the present invention is not particularly limited. One or combination of two or more of the polymerizable triptycene derivatives of the general formula (1) may be subjected to a polymerization reaction to obtain a polymer composition. Similarly, one or combination of two or more of the polymerizable triptycene derivatives of the general formula (1)' may be subjected to a polymerization reaction to obtain a polymer composition.

In the resulting polymer composition obtained by using any of the polymerizable triptycene derivatives according to one embodiment of the present invention, each of the three benzene rings in the triptycene structure can rotate evenly about the axis formed by barrelene and the introduced polymerizable functional groups are hydrophilic groups. Thus, the polymer composition can encapsulate a hydrophilic material or a hydrophobic material and it is possible to control the rate and the extent of diffusion of the encapsulated material when it is released from the polymer composition. The polymer composition with such characteristics can be used in a variety of applications, including, for example, liquid crystal alignment film, liquid crystal display elements, organic EL displays, organic thin films with electron transporting properties, light-emitting elements and organic conductive compositions, as well as hydrogels, medical devices, ophthalmic lenses and DDS devices.

The present invention will now be described more specifically with reference to the following Examples, which are not intended to limit the present invention. The present invention may take various forms to the extent that the objectives of the present invention are achieved.

EXAMPLES

Example 1. Synthesis of Triptycene Derivative (14)

1. Synthesis Scheme for Triptycene Derivative (14)

A triptycene derivative compound (14) was synthesized according to the following Scheme (I):

[Chemical formula 16]

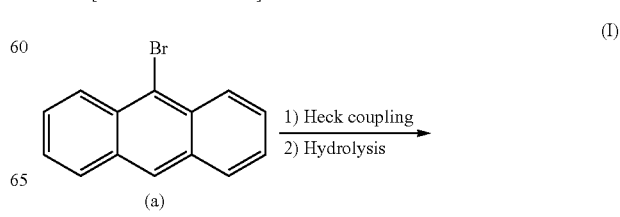

(I)

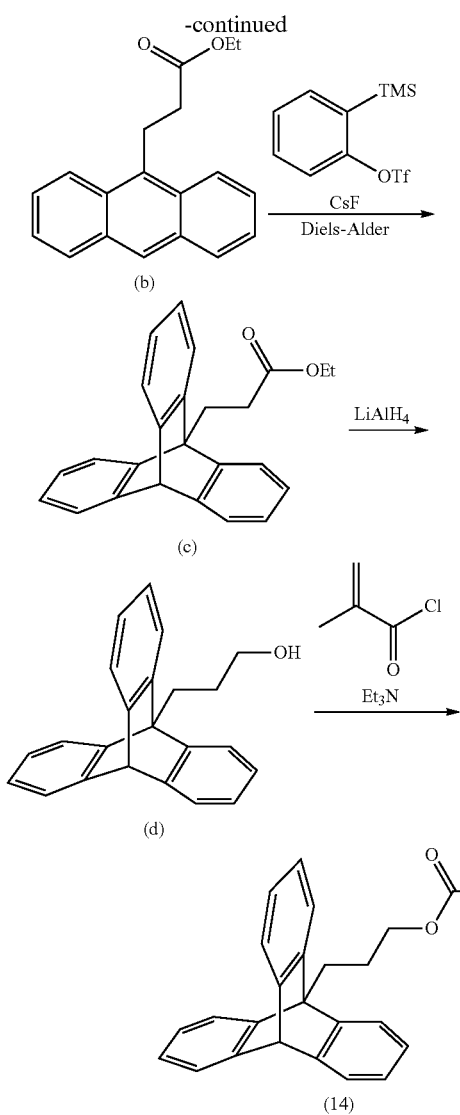

2. Synthesis of Compound (b)

Compound (b) in Scheme (I) was synthesized according to a method described in Ke Pan, et al., Journal of Organometallic Chemistry, 2008; 693(17); p. 2863-2868, the disclosure of which is incorporated herein by reference in its entirety. Specifically, to a dimethylformamide solution (30 ml) of 2.7 g (10 mmol) of compound (a), which is 9-bromoanthracene, 0.19 g (0.2 mmol) of Herrmann's palladacycle, 2.1 g (15 mmol) of potassium carbonate, and 2.3 mL (15 mmol) acrolein diethyl acetal were added under an argon atmosphere at room temperature and the mixture was stirred overnight at 110° C. to allow the reaction to proceed. The resulting reaction mixture was allowed to cool to room temperature and diluted with ethyl acetate. This was followed by washing with 1N hydrochloric acid, a saturated aqueous sodium bicarbonate solution and a saturated brine. The separated organic layer was dried over anhydrous magnesium sulfate and the solvent was removed by evaporation. The resulting residue was purified by silica gel column chromatography to obtain 2.4 g (87% yield) of compound (b).

3. Synthesis of Compound (c)

To a solution of 0.87 g (3.1 mmol) of compound (b) dissolved in 15 ml acetonitrile, 0.57 g (3.7 mmol) of cesium fluoride and 0.91 mL (3.7 mmol) 2-(trimethylsilyl)phenyl triflate were added under an argon atmosphere and the mixture was stirred at 40° C. for 18 hours. After stirring, the reaction mixture was allowed to cool to room temperature and filtrated through Celite. The resulting filtrate was concentrated under reduced pressure. The resulting residue was purified by silica gel column chromatography to obtain 0.92 g (83% yield) of compound (c).

NMR spectra for the resulting compound (c) were as follows:

$^1$H-NMR (CDCl$_3$) δppm; 1.35 (t, 3H), 3.17 (m, 2H), 3.35 (m, 2H), 4.31 (q, 2H), 5.35 (s, 1H), 7.00 (m, 6H), 7.37 (m, 6H).

$^{13}$C-NMR (CDCl$_3$) δppm; 14.47, 22.61, 30.96, 53.48, 54.58, 61.01, 122.12, 123.7 0, 125.02, 125.14, 145.76, 146.99, 174.20.

4. Synthesis of Compound (d)

0.051 g (1.3 mmol) of lithium aluminum hydride was dissolved in 10 mL tetrahydrofuran chilled to 0° C. under an argon atmosphere to form a solution. To the resulting solution, 0.40 g (1.1 mmol) of compound (c) was added and the mixture was stirred for three hours at room temperature. While the resulting reaction mixture was chilled on ice, 0.05 mL water, a 0.05 mL 15 w/v % aqueous sodium hydroxide solution, and 0.15 mL water were sequentially added dropwise slowly and the mixture was stirred for one hour at room temperature. After stirring, the reaction mixture was filtrated through Celite. The resulting filtrate was concentrated under reduced pressure. The resulting residue was purified by silica gel column chromatography to obtain 0.22 g (62% yield) of compound (d).

NMR spectra for the resulting compound (d) were as follows:

$^1$H-NMR (CDCl$_3$) δppm; 2.41 (m, 2H), 2.98 (m, 2H), 4.00 (t, 2H), 5.34 (s, 1H), 6.96 (m, 6H), 7.36 (m, 6H).

$^{13}$C-NMR(CDCl$_3$) δppm; 24.36, 28.23, 53.29, 54.63, 64.00, 122.44, 123.60, 124.88, 124.98, 146.33, 147.07.

5. Synthesis of Triptycene Derivative (14)

To a solution of 0.22 g (0.70 mmol) of compound (d) dissolved in 10 mL tetrahydrofuran, 0.15 mL (1.1 mmol) triethylamine and 0.10 mL (1.1 mmol) methacryloyl chloride were added under an argon atmosphere at 0° C. and the mixture was stirred at 0° C. for 18 hours. After stirring, the reaction was quenched by adding a saturated aqueous sodium bicarbonate solution and the organic compound in the solution was extracted with diethyl ether. The extracted organic layer was washed with saturated brine and dried with anhydrous magnesium sulfate. The solvent was then removed from the dried organic layer by evaporation and the resulting residue was purified by silica gel column chromatography to obtain 0.16 g (60% yield) of a triptycene derivative (14).

NMR spectra for the resulting triptycene derivative (14) were as follows: Also, the triptycene derivative (14) was subjected to a polymerization reaction to give a polymer composed of the triptycene derivative (14) as its structural units.

$^1$H-NMR (CDCl$_3$) δppm; 2.04 (s, 3H), 2.60 (m, 2H), 3.04 (m, 2H), 4.58 (t, 2H), 5.36 (s, 1H), 5.63 (m, 1H), 6.25 (s, 1H), 6.99 (m, 6H), 7.39 (m, 6H).

$^{13}$C-NMR(CDCl$_3$) δppm; 18.60, 24.53, 24.57, 53.15, 54.62, 65.64, 122.28, 123.6 8, 124.91, 125.07, 125.85, 136.50, 146.09, 147.04, 167.77.

Example 2. Synthesis of Triptycene Derivative (15)

1. Synthesis Scheme for Triptycene Derivative (15)

A triptycene derivative (15) was synthesized according to the following Scheme (II):

[Chemical formula 17]

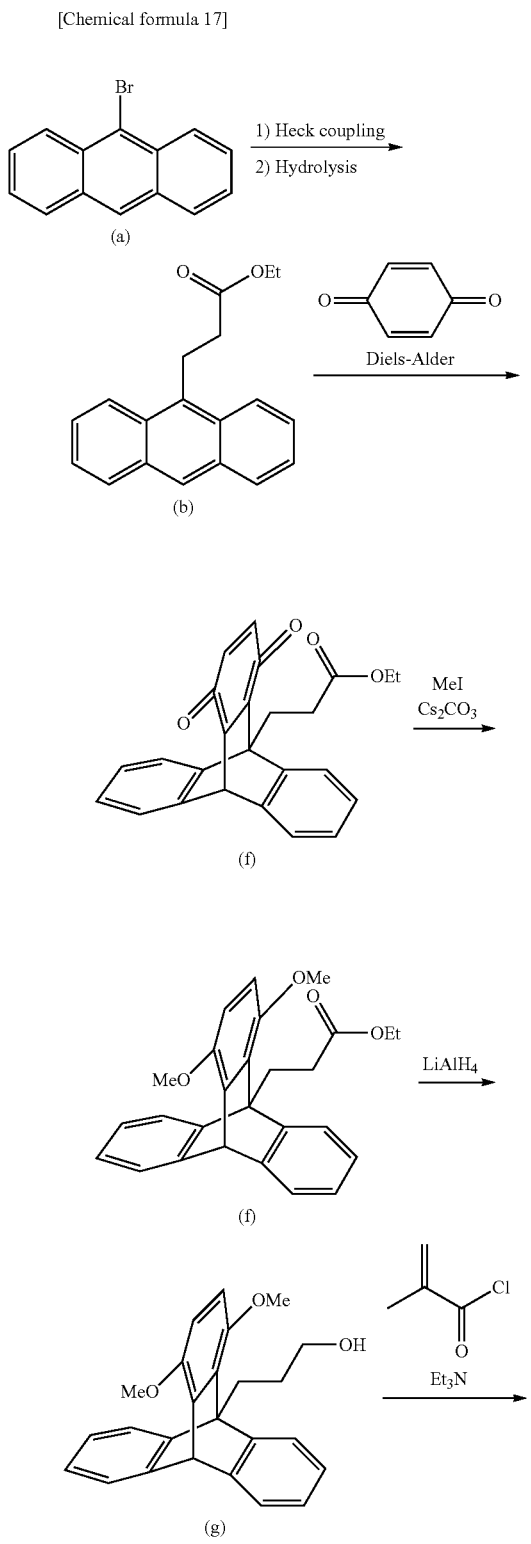

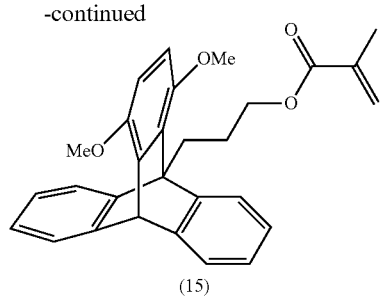

2. Synthesis of Compound (b)

Compound (b) was synthesized with reference to "2. Synthesis of compound (b)" in Example 1.

3. Synthesis of Compound (e)

To a solution of 1.1 g (10 mmol) of benzoquinone dissolved in 15 mL dichrolomethane, 1.1 mL (9.0 mmol) of a boron trifluoride-diethyl ether complex was added under an argon atmosphere at 0° C. and the mixture was stirred for 30 min. After stirring, the reaction mixture was cooled to −20° C. To the cooled reaction mixture, 0.56 g (2.0 mmol) of compound (b) was added and the mixture was stirred for three hours at −20° C. After stirring, the reaction mixture was allowed to cool to room temperature and washed with saturated brine. The organic layer separated from the washed reaction mixture was then dried over anhydrous magnesium sulfate. The solvent was removed from the dried organic layer by evaporation and the resulting residue was purified by silica gel column chromatography to obtain 0.67 g (87% yield) of compound (e).

NMR spectra for the resulting compound (e) were as follows:

$^1$H-NMR (CDCl$_3$) δppm; 1.37 (t, 3H), 2.80 (m, 2H), 2.90 (m, 1H), 2.99 (d, 1H), 3.22 (dd, 1H), 3.34 (m, 1H), 4.29 (dd, 2H), 4.65 (d, 1H), 6.12 (d, 2H), 7.18 (m, 6H), 7.41 (m, 2H).

$^{13}$C-NMR (CDCl$_3$) δppm; 14.48, 24.00, 30.22, 49.38, 50.10, 51.05, 60.86, 122.24, 123.17, 124.20, 124.93, 126.63, 126.73, 126.85, 127.06, 139.03, 140.0 5, 141.37, 141.88, 142.98, 173.85, 197.73, 198.89.

4. Synthesis of Compound (f)

To a solution of 0.93 g (2.4 mmol) of compound (e) dissolved in 10 mL dimethylformamide, 2.0 g (6.0 mmol) of cesium carbonate and 0.67 mL (7.2 mmol) methyl iodide were added under an argon atmosphere and the mixture was stirred at 40° C. for 18 hours. After stirring, the reaction mixture was filtered through Celite. The resulting filtrate was concentrated under reduced pressure and the resulting concentrated residue was purified by silica gel column chromatography to obtain 0.82 g (82% yield) of compound (f).

NMR spectra for the resulting compound (f) were as follows:

$^1$H-NMR (CDCl$_3$) δppm; 1.37 (t, 3H), 3.09 (br s, 2H), 3.66 (s, 3H), 3.74 (br s, 2H), 3.80 (s, 3H), 4.29 (q, 2H), 5.86 (s, 1H), 6.51 (m, 2H), 7.01 (m, 4H), 7.43 (m, 4H).

$^{13}$C-NMR (CDCl$_3$) δppm; 14.52, 24.23, 32.65, 32.71, 47.27, 56.08, 56.50, 60.47, 109.73, 110.23, 123.47, 123.79, 124.78, 125.21, 125.55, 146.50, 148.86, 150.17, 174.92.

5. Synthesis of Compound (g)

The same procedure was followed as in "4. Synthesis of compound (d)" in Example 1, except that 0.69 g (1.7 mmol) of compound (f) was used in place of compound (c) to obtain 0.58 g (93% yield) of compound (g).

NMR spectra for the resulting compound (g) were as follows:

$^1$H-NMR (CDCl$_3$) δppm; 1.65 (br s, 1H), 2.34 (br s, 2H), 3.28 (br s, 2H), 3.70 (s, 3H), 3.79 (s, 3H), 4.05 (t, 2H), 5.85 (s, 1H), 6.50 (m, 2H), 7.01 (m, 4H), 7.46 (m, 4H).

$^{13}$C-NMR(CDCl$_3$) δppm; 26.06, 29.85, 29.99, 47.38, 56.56, 56.60, 64.70, 109.68, 110.72, 123.76, 124.66, 124.91, 146.67, 148.94, 150.45.

6. Synthesis of Triptycene Derivative (15)

The same procedure was followed as in "5. Synthesis of triptycene derivative (14)" in Example 1, except that 0.50 g (1.3 mmol) of compound (g) was used in place of compound (d) to obtain 0.51 g (87% yield) of triptycene derivative (15).

NMR spectra for the resulting triptycene derivative (15) were as follows. Also, the triptycene derivative (15) was subjected to a polymerization reaction to give a polymer composed of the triptycene derivative (15) as its structural units.

$^1$H-NMR (CDCl$_3$) δppm; 2.04 (m, 3H), 2.47 (br s, 2H), 3.33 (br s, 2H), 3.70 (s, 3H), 3.78 (s, 3H), 4.54 (t, 2H), 5.62 (m, 1H), 5.86 (s, 1H), 6.23 (d, 1H), 6.50 (br s, 2H), 7.02 (m, 4H), 7.41 (br s, 2H), 7.50 (br s, 2H).

$^{13}$C-NMR(CDCl$_3$) δppm; 18.59, 25.91, 26.30, 47.35, 54.86, 56.32, 56.54, 66.33, 109.66, 110.47, 123.78, 124.66, 124.96, 125.54, 136.70, 138.11, 146.66, 148.88, 150.37, 167.87.

Example 3. Synthesis of Triptycene Derivative (16)

1. Synthesis Scheme for Triptycene Derivative (16)

A triptycene derivative (16) was synthesized according to the following Scheme (III):

[Chemical Formula 18]

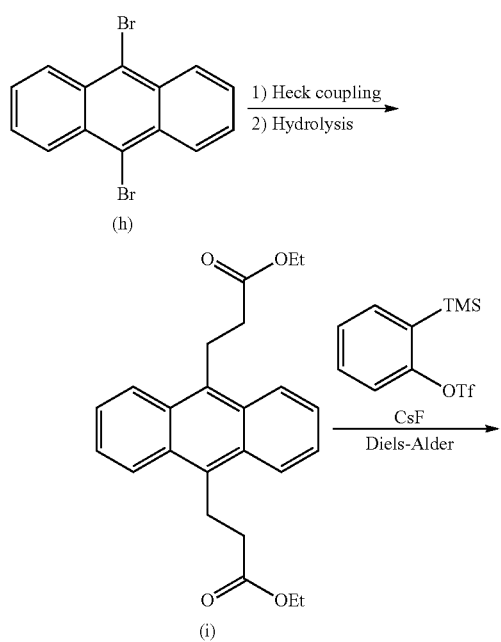

(III)

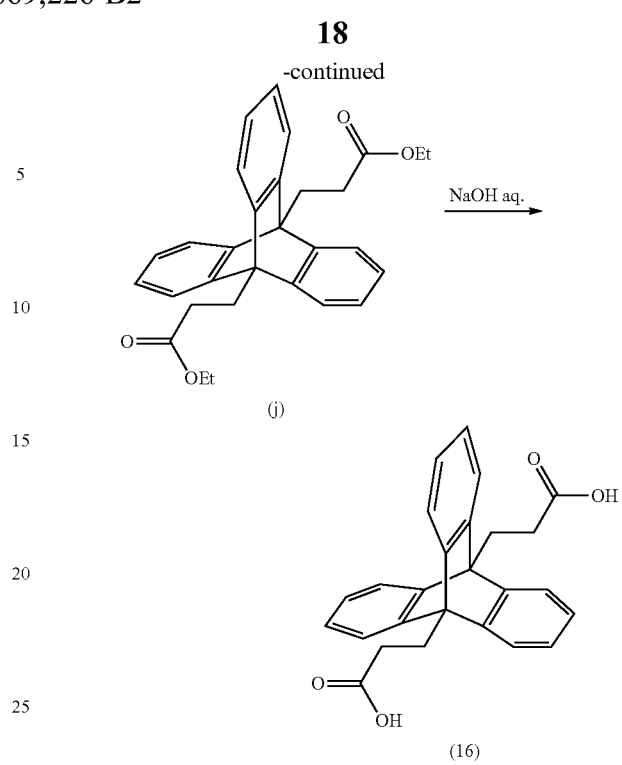

2. Synthesis of Compound (i)

The same procedure was followed as in "2. Synthesis of compound (b)" in Example 1, except that 1.68 g (10 mmol) of compound (h), 9,10-dibromoanthracene, was used in place of compound (a) to obtain 1.19 g (63% yield) of compound (i).

3. Synthesis of Compound (j)

The same procedure was followed as in "3. Synthesis of compound (c)" in Example 1, except that 0.26 g (0.69 mmol) of compound (i) was used in place of compound (b) to obtain 0.29 g (93% yield) of compound (j).

NMR spectra for the resulting compound (j) were as follows:

$^1$H-NMR (CDCl$_3$) δppm; 1.36 (m, 6H), 3.16 (m, 4H), 3.34 (m, 4H), 4.33 (q, 4H), 7.02 (m, 6H), 7.40 (m, 6H).

$^{13}$C-NMR (CDCl$_3$) δppm; 14.47, 22.75, 31.03, 52.76, 61.04, 122.19, 124.88, 146.91, 174.18.

4. Synthesis of Triptycene Derivative (16)

A solution of 0.26 g (0.58 mmol) of compound (j) dissolved in 10 mL of 15 w/v % sodium hydroxide/ethanol (1:1) was heated to reflux at 80° C. for five hours. The resulting reaction mixture was allowed to cool to room temperature and the solvent was removed by evaporation under reduced pressure. To the resulting residue, 1 N hydrochloric acid was added to adjust the pH to 5 and the resulting organic material was extracted with chloroform three times. The resulting organic layer was washed with saturated brine and dried with anhydrous sodium sulfate. The solvent was then removed from the dried organic layer by evaporation and the resulting residue was purified by silica gel column chromatography to obtain 0.20 g (85% yield) of a triptycene derivative (16).

NMR spectra for the resulting triptycene derivative (16) were as follows. Also, the triptycene derivative (16) was subjected to a polymerization reaction to give a polymer composed of the triptycene derivative (16) as its structural units.

¹H-NMR (DMSO-d6) δppm; 3.01 (m, 4H), 3.20 (m, 4H), 7.04 (m, 6H), 7.38 (m, 6H), 12.48 (s, 2H).

¹³C-NMR (DMSO-d6) δppm; 21.76, 30.40, 52.56, 121.81, 124.66, 147.10, 174.84.

Example 4. Synthesis of Triptycene Derivative (17)

1. Synthesis Scheme for Triptycene Derivative (17)

A triptycene derivative (17) was synthesized according to the following Scheme (IV):

[Chemical Formula 19]

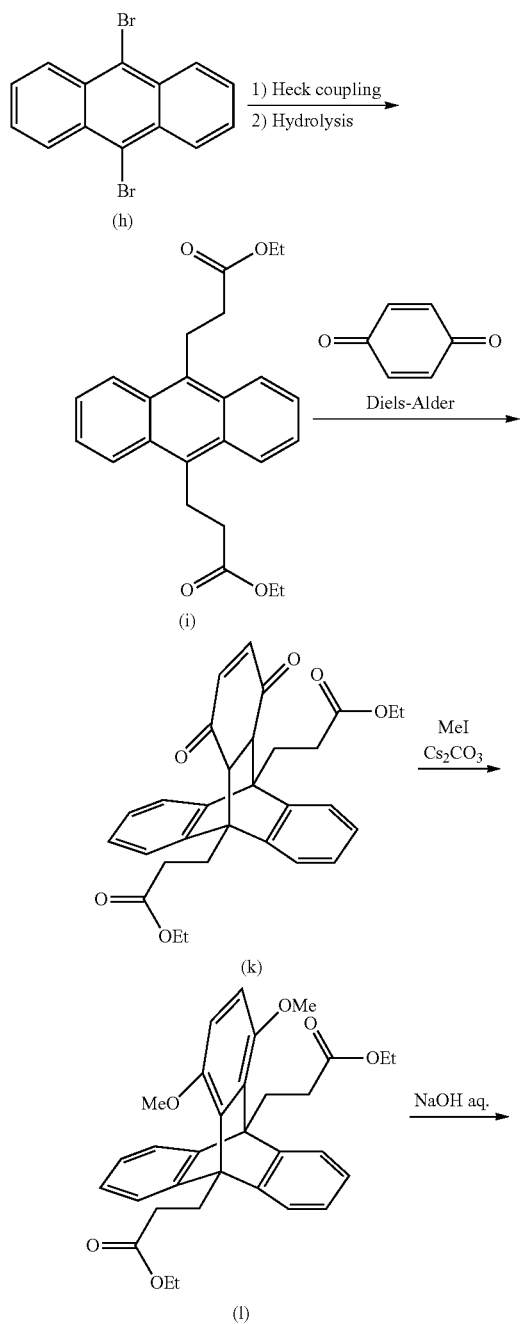

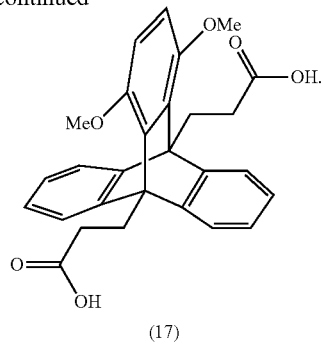

2. Synthesis of Compound (i)

Compound (i) was synthesized with reference to "2. Synthesis of compound (i)" in Example 3.

3. Synthesis of Compound (k)

The same procedure was followed as in "3. Synthesis of compound (e)" in Example 2, except that 0.76 g (2.0 mmol) of compound (i) was used in place of compound (b) to obtain 0.87 g (89% yield) of compound (k).

NMR spectra for the resulting compound (k) were as follows:

¹H-NMR (CDCl₃) δppm; 1.36 (t, 6H), 2.61 (m, 2H), 2.88 (m, 4H), 3.10 (s, 2H), 3.38 (m, 2H), 4.29 (q, 4H), 5.99 (s, 2H), 7.22 (m, 6H), 7.41 (dd, 2H).

¹³C-NMR(CDCl₃) δppm; 14.43, 24.30, 29.78, 47.59, 51.31, 60.96, 122.18, 123.2 7, 126.46, 126.91, 139.80, 143.23, 173.76, 197.59.

4. Synthesis of Compound (1)

The same procedure was followed as in "4. Synthesis of compound (f)" in Example 2, except that 1.2 g (2.6 mmol) of compound (k) was used in place of compound (e) to obtain 1.2 g (92% yield) of compound (1).

NMR spectra for the resulting compound (1) were as follows:

¹H-NMR (CDCl₃) δppm; 1.33 (t, 6H), 2.97 (m, 6H), 3.70 (s, 6H), 3.77 (m, 2H), 4.27 (m, 4H), 6.60 (s, 2H), 7.00 (m, 4H), 7.41 (m, 4H).

¹³C-NMR(CDCl₃) δppm; 14.54, 24.81, 32.43, 52.97, 56.09, 60.41, 110.78, 120.7 8, 123.18, 124.06, 125.26, 134.89, 148.68, 149.08, 149.87, 174.99.

5. Synthesis of Triptycene Derivative (17)

The same procedure was followed as in "4. Synthesis of triptycene derivative (16)" in Example 3, except that 0.10 g (0.2 mmol) of compound (1) was used in place of compound (j) to obtain 0.078 g (88% yield) of triptycene derivative (17).

NMR spectra for the resulting triptycene derivative (17) were as follows: Also, the triptycene derivative (17) was subjected to a polymerization reaction to give a polymer composed of the triptycene derivative (17) as its structural units.

¹H-NMR (DMSO-d6) δppm; 2.82 (m, 6H), 3.63 (m, 8H), 6.65 (d, 2H), 7.02 (m, 4H), 7.43 (m, 4H), 12.22 (s, 2H).

¹³C-NMR (DMSO-d6) δppm; 24.33, 31.82, 52.47, 55.63, 110.65, 120.36, 123.14, 123.35, 123.95, 124.89, 125.12, 133.77, 145.99, 148.50, 148.79, 149.26, 149.91, 17 5.27.

Example 5. Synthesis of Triptycene Derivative (18)

1. Synthesis Scheme for Triptycene Derivative (18)

A triptycene derivative (18) was synthesized according to the following Scheme (V):

[Chemical Formula 20]

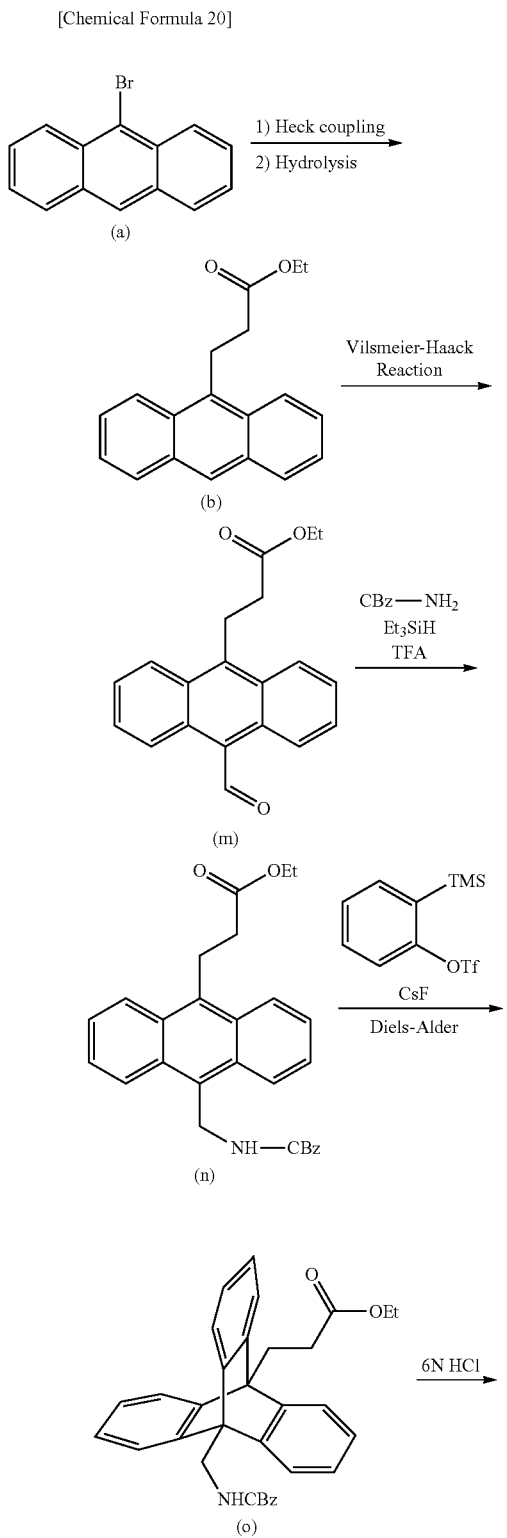

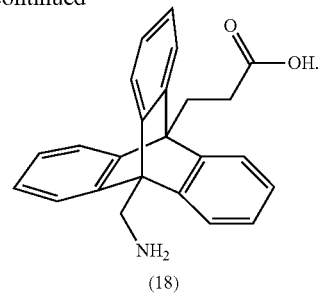

2. Synthesis of Compound (b)

Compound (b) was synthesized with reference to "2. Synthesis of compound (b)" in Example 1.

3. Synthesis of Compound (m)

To 5 mL of dimethylformamide, 0.94 mL (10.1 mmol) phosphoryl chloride was added dropwise under an argon atmosphere at 0° C. and the mixture was stirred at room temperature for 1.5 hours. To the stirred reaction mixture, 1.0 g (3.6 mmol) of compound (b) was dissolved and the mixture was stirred at 110° C. for 18 hours. After stirring, the reaction mixture was allowed to cool to room temperature and diluted with ethyl acetate. The diluted reaction mixture was sequentially washed with 1N hydrochloric acid, a saturated aqueous sodium bicarbonate solution and a saturated brine. The organic layer separated after washing was dried over anhydrous magnesium sulfate. The solvent was removed from the dried organic layer by evaporation and the resulting residue was purified by silica gel column chromatography to obtain 0.78 g (71% yield) of compound (m).

NMR spectra for the resulting compound (m) were as follows:

$^1$H-NMR (CDCl$_3$) δppm; 1.25 (m, 3H), 2.77 (m, 2H), 3.98 (m, 2H), 4.20 (q, 2H), 7.62 (m, 4H), 8.33 (m, 2H), 8.92 (dd, 2H), 11.45 (s, 1H).

$^{13}$C-NMR(CDCl$_3$) δppm; 14.34, 24.19, 35.32, 60.99, 124.45, 124.77, 125.01, 126.30, 128.48, 129.08, 131.64, 141.68, 172.65, 193.63.

4. Synthesis of Compound (n)

To a solution of 0.74 g (2.4 mmol) of compound (m) dissolved in 10 ml acetonitrile, 1.1 g (7.2 mmol) of benzyl carbamate, 0.59 mL (7.2 mmol) triethylsilane, and 0.61 mL (7.0 mmol) of trifluoroacetic acid were added under an argon atmosphere and the mixture was stirred at room temperature for 18 hours. After stirring, the reaction mixture was diluted with ethyl acetate and was sequentially washed with a saturated aqueous sodium bicarbonate solution and a saturated brine. The organic layer separated after washing was dried over anhydrous magnesium sulfate. The solvent was removed from the dried organic layer by evaporation and the resulting residue was purified by silica gel column chromatography to obtain 0.84 g (83% yield) of compound (n).

NMR spectra for the resulting compound (n) were as follows:

$^1$H-NMR(CDCl$_3$) δppm; 1.21 (m, 3H), 2.69 (m, 2H), 3.90 (m, 2H), 4.13 (q, 2H), 4.94 (s, 1H), 5.08 (s, 2H), 5.32 (d, 2H), 7.28 (m, 5H), 7.50 (m, 4H), 8.27 (m, 4H).

$^{13}$C-NMR(CDCl$_3$) ppm; 14.36, 23.60, 35.40, 37.73, 60.84, 67.00, 124.84, 125.8 2, 126.36, 128.16, 128.60, 129.38, 130.19, 134.17, 136.52, 156.23, 173.02.

5. Synthesis of Compound (o)

The same procedure was followed as in "3. Synthesis of compound (c)" in Example 1, except that 0.29 g (0.66 mmol)

of compound (m) was used in place of compound (b) to obtain 0.27 g (78% yield) of compound (o).

NMR spectra for the resulting compound (o) were as follows:

$^1$H-NMR (CDCl$_3$) δppm; 1.36 (m, 3H), 3.14 (m, 2H), 3.34 (m, 2H), 4.33 (q, 2H), 4.85 (d, 2H), 5.26 (s, 2H), 5.42 (m, 1H), 7.03 (m, 6H) 7.35 (m, 11H).

$^{13}$C-NMR(CDCl$_3$) δppm; 14.48, 22.68, 30.97, 40.20, 52.03, 52.92, 61.11, 67.19, 122.35, 125.26, 128.20, 128.33, 128.69, 136.58, 147.07, 156.59, 174.08.

6. Synthesis of Triptycene Derivative (18)

A solution of 0.23 g (0.44 mmol) of compound (o) dissolved in 10 mL of 15 w/v % sodium hydroxide/ethanol (1:1) was heated to reflux at 80° C. for five hours. The resulting reaction mixture was allowed to cool to room temperature and the solvent was removed by evaporation under reduced pressure. To the resulting residue, 1 N hydrochloric acid was added to adjust the pH to 5 and the resulting organic material was extracted with chloroform three times. The resulting organic layer was dried over anhydrous sodium sulfate. The solvent was removed from the dried organic layer by evaporation and the resulting residue was dissolved in 10 mL methanol. To this solution, 0.04 g of 10 w/w % palladium on carbon was added and the mixture was vigorously stirred under a hydrogen atmosphere at room temperature. The solvent was then removed from the resulting solution by evaporation and the resulting residue was subjected to recrystallization from water/ethanol to obtain 0.12 g (79% yield) of a triptycene derivative compound (18).

NMR spectra for the resulting triptycene derivative compound (18) were as follows. Also, the triptycene derivative compound (18) was subjected to a polymerization reaction to give a polymer composed of the triptycene derivative compound (18) as its structural units.

$^1$H-NMR (DMSO-d6) δppm; 2.34 (m, 2H), 2.56 (m, 2H), 3.80 (s, 2H), 6.38 (s, 6H), 6.81 (m, 6H), 9.01 (br s, 2H).

$^{13}$C-NMR (DMSO-d6) δppm; 21.79, 30.46, 36.62, 48.70, 52.81, 122.13, 124.92, 125.31, 144.71, 174.80.

INDUSTRIAL APPLICABILITY

The polymerizable triptycene derivative in one embodiment of the present invention can be used as materials in a variety of applications, including, for example, liquid crystal alignment films, liquid crystal display elements, organic EL displays, organic thin films with electron transporting properties, light-emitting elements and organic conductive compositions, as well as hydrogels, medical devices, ophthalmic lenses and DDS devices.

The invention claimed is:

1. A polymerizable triptycene derivative represented by the following general formula (1):

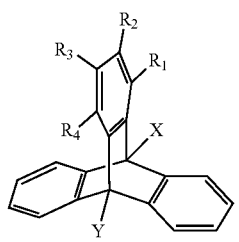

(1)

wherein

R$_1$ to R$_4$ are each independently a substituent selected from the group consisting of hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group, with the proviso that adjacent substituents may together form a ring;

one of X and Y is a substituent represented by the following general formula (2):

(2)

(wherein n is an integer of 1 to 5; and R$_5$ is a substituent selected from the group consisting of alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group, each having an unsaturated polymerizable functional group;)

and the other of X and Y is a substituent selected from the group consisting of the substituents represented by the general formula (2), hydrogen atom and halogen atom, and protected or unprotected hydroxyl group, hydroxylalkyl group, carboxyl group, carboxylalkyl group, amino group, aminoalkyl group, aminocarbonyl group, aminocarbonylalkyl group, alkoxy group, alkoxyalkyl group, alkoxycarbonyl group, alkoxycarbonylalkyl group, formyl group, formylalkyl group, and alkyl group.

2. The polymerizable triptycene derivative according to claim 1, wherein said unsaturated polymerizable functional group is an unsaturated polymerizable functional group selected from the group consisting of vinyl group and (meth)acryl group.

3. A polymerizable triptycene derivative represented by the following general formula (1)':

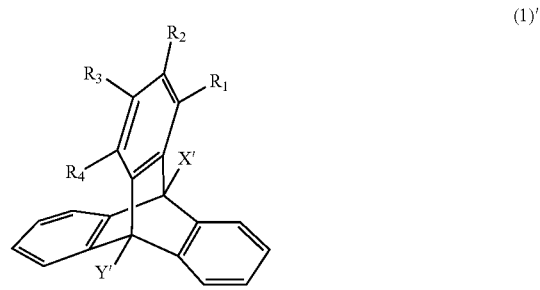

(1)' wherein

R$_1$ to R$_4$ are each independently a substituent selected from the group consisting of hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, carbonyl group, carboxyl group, oxycarbonyl group, carbamoyl group, amino group, phosphineoxide group, and silyl group, with the proviso that adjacent substituents may together form a ring;

one of X' and Y' is a substituent represented by the following general formula (3):

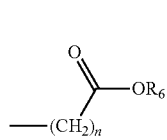

(3)

wherein n is an integer of 1 to 5; and $R_6$ is a substituent selected from the group consisting of hydrogen atom and alkyl group having any one of carbons 1 to 3;

and the other of X' and Y' is a substituent represented by the following general formula (4):

$$—(CH_2)_n—NHR_7 \qquad (4)$$

wherein n is an integer of 1 to 5; and $R_7$ is a substituent selected from the group consisting of hydrogen atom and a carbamate protective group.

* * * * *